Nov. 14, 1933. B. E. BAUER ET AL Plant Pat. 82
THORNLESS LOGAN BLACKBERRY
Filed Sept. 6, 1932
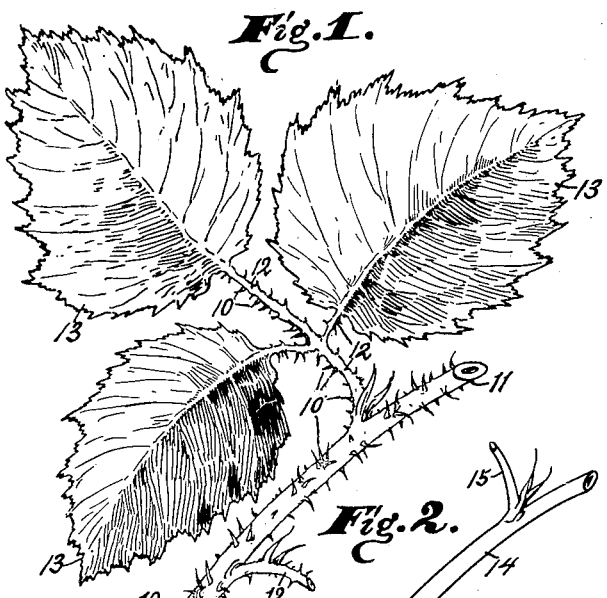
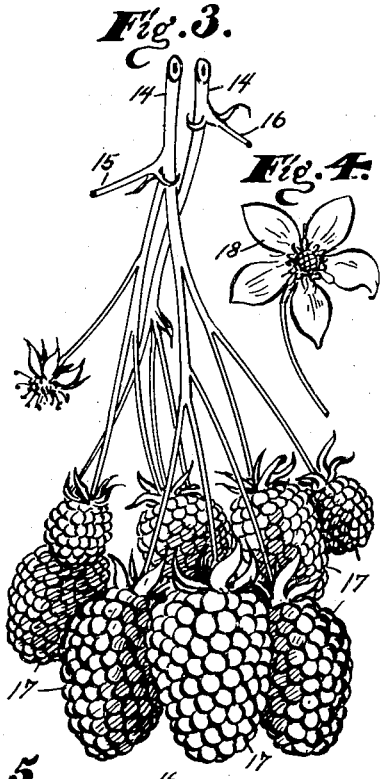
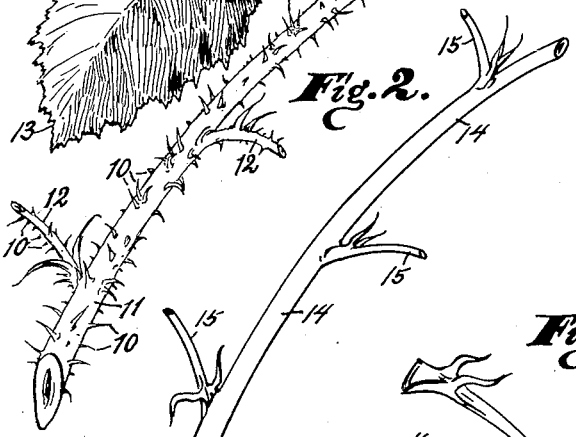
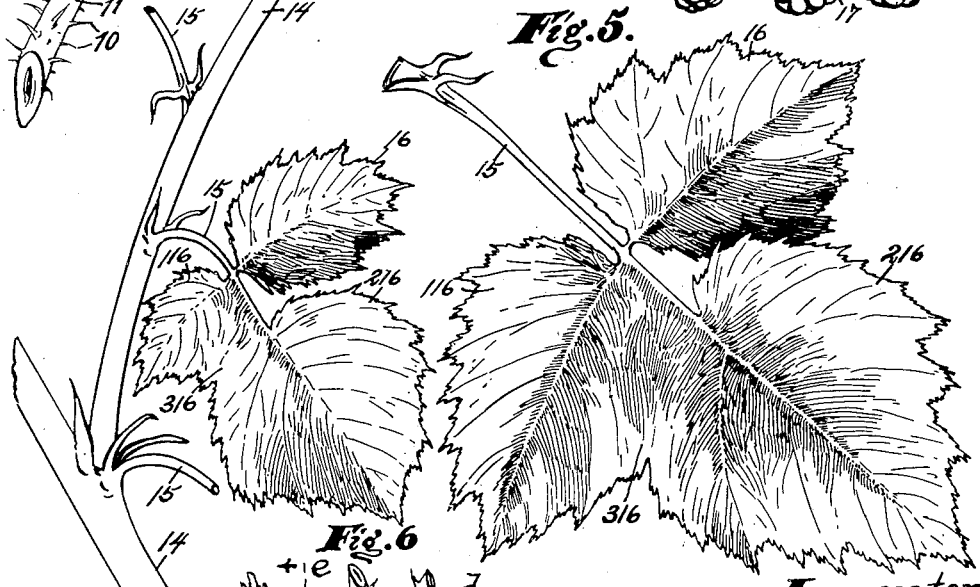
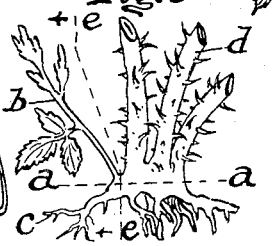
Inventors.
Beulah E. Bauer.
Gordon R. Bauer.
By
William M. Gentle
Their Attorney.

Patented Nov. 14, 1933

UNITED STATES PATENT OFFICE

82

THORNLESS LOGAN BLACKBERRY

Beulah E. Bauer and Gordon R. Bauer,
San Gabriel, Calif.

Application September 6, 1932. Serial No. 631,852

1 Claim. (Cl. 47—1)

This discovery is a new variety of thornless Logan blackberry having large, strong and relatively nonbrittle canes, the fruit of which is larger than, but similar as to color and taste to, the fruit of the Logan blackberry from which this new variety has been propagated. Also this new variety is further distinguished from the parent variety in the respect that it bears longer and is more prolific.

This new variety was discovered by us as a sport that was growing from a cane of a Logan blackberry plant and from its first appearance indicated an individual variation from the parent stock or cane in the respect that it was thornless.

This sport was discovered in our garden in the city of San Gabriel, county of Los Angeles, and State of California, growing on one of the plants of a row of Logan blackberries, and immediately after this discovery we held a consultation, and concluded to begin a propagation of this sport to see if it would retain permanently its thornless character.

This propagation included cutting away at once the thorny portion of the parent Logan blackberry plant and all of the roots thereof, except that to which the sport was directly connected. This sport was then cultivated until it grew to the usual length and spread of an ordinary Logan blackberry plant, and at the proper time, in September 1930, we laid the tips of this thornless cane in the ground to develop a new variety which, when developed and replanted in the spring of 1931, grew into thornless plants, some of which bore fruit that year which, as to size, color and taste resembled the fruit of the parent plant, except that its fruiting period began much earlier than Logan blackberries growing in the same garden under like conditions, and continued in full fruitage much longer than the Logan blackberries.

In September of 1931 we again laid the tips of the thornless canes developed from the thornless sport which we discovered, and in the spring of 1932 we planted and cultivated the plants developed by the 1931 tipping; and all of these plants grew true to the sport in the respect that they are entirely thornless, and from this development we are assured that the thornless characteristic of this new variety is permanent.

In the accompanying drawing the new variety of Logan blackberry, together with its fruit and foliage is illustrated, which illustration was made by the artist from cuttings taken from plants growing in our garden showing the parent Logan blackberry cane and also a cane of the new variety.

In the drawing:

Figure 1 shows a cutting from the parent Logan blackberry cane with the thorns of the cane and leaf stems placed as true to size and position as the artist could make them.

Fig. 2 shows a cutting from the new thornless variety and also illustrating one of the characteristics of its foliage.

Fig. 3 is a perspective view of a cluster of fruit taken from the canes of the new variety showing the stems entirely thornless.

Fig. 4 is a blossom of the new variety also showing its stem as thornless.

Fig. 5 is a perspective view of one of the thornless leaves pulled from a cane of this new Thornless Logan Blackberry.

Fig. 6 is a diagrammatic fragmental view of a Logan blackberry plant illustrating how the thornless sport was discovered and the thorny portion of the plant cut away to leave the sport with its root growing in the ground In detail the parent plant or Logan blackberry cane as illustrated in Fig. 1 is excessively thorny with the thorns 10 not only covering the cane 11, but also extending along the undersides of the stems 12 of the leaves 13. Also, as is well understood, the ribs of the Logan blackberry leaves have a great many thorns of considerable size on their underside, not shown in the drawing, that make the handling of the canes very difficult.

As seen in Fig. 2, the new cane 14 is thornless and also its stems 15 and leaves 16, are entirely thornless, in addition to which the cane appears to be slightly larger and stronger and less brittle than the parent cane, and can be handled without gloves and its position changed, as when tying it up to a stake, without danger of its breaking.

Also we have noted that the foliage of this new variety appears to be slightly larger and more vigorous in growth than the parent variety; and also we have observed that many of the leaves instead of being clearly separated in triplet form on a stem, as illustrated in Fig. 1, are inclined to grow as illustrated in Figs. 2 and 5, which is characteristic of the parent variety, although not shown in the drawing.

In other words, as illustrated in Fig. 5, only the leaf 16 on stem 15 is separate, and the other two leaves 116 and 216 of the triplet are grown together at 316 in twin form. Of course it is understood that not all of the leaves grow in this manner, but sufficient to make this unusual growth of foliage noticeable in both the parent stock and sport.

In Fig. 6 the dotted line *a—a* indicates the top surface of the ground, and *b* indicates our newly discovered thornless sport growing out from the root *c*, and *d* indicates the parent Logan blackberry plant, and the line *e—e* indicates how the sport *b* was separated from the plant. The parent plant on the right side of the line *e—e* was cut away and the roots removed so that the sport on the left side of the line *e—e* could be developed alone, which process of development has heretofore been described.

As previously indicated, the fruit 17 of the new variety as respecting taste and color, is like the fruit of the parent Logan blackberry except that as to size they appear to be slightly larger, and begin ripening a few days earlier and remain in bearing a few days longer than that of the parent variety, and, so far as we can determine from our propagation, they are more prolific than the parent Logan blackberry.

The flower 18 of the new variety, as shown in Fig. 4, is like the blossoms of the parent variety, except that the stems are thornless.

The exceptionally strong, hardy and non-brittle canes of this new plant, in addition to its longer and more prolific fruitage, indicates that it is an entirely new variety of Logan blackberry.

Also as previously indicated, this new thornless variety of Logan blackberry has been under the course of propagation and development since 1929 and is now fully established as a new and useful variety of plant that appears to be patentable as now provided for in the United States Patent Office.

What we claim and desire to secure by Letters Patent is:

A thornless variety of Logan blackberry herein shown and described, characterized particularly by its large growth of large non-brittle canes and heavy foilage with its canes, leaves and stems entirely thornless, and also characterized by an early, longer and more prolific bearing period with the berries larger than those of the common Logan blackberry.

BEULAH E. BAUER.
GORDON R. BAUER.